United States Patent
Lee et al.

(10) Patent No.: US 11,878,295 B2
(45) Date of Patent: Jan. 23, 2024

(54) NANOCATALYST FOR PARTIAL OXIDATION OF METHANE, METHOD FOR PREPARING THE NANOCATALYST AND METHOD FOR PARTIAL OXIDATION OF METHANE USING THE NANOCATALYST

(71) Applicant: INDUSTRY-ACADEMIC COOPERATION FOUNDATION, YONSEI UNIVERSITY, Seoul (KR)

(72) Inventors: Sang-Yup Lee, Seoul (KR); Hyesung Lee, Seoul (KR); Jeewon Ju, Daejeon (KR); Junsang Lee, Seoul (KR); Sukjun Lee, Gyeonggi-do (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 17/851,193

(22) Filed: Jun. 28, 2022

(65) Prior Publication Data
US 2023/0139887 A1    May 4, 2023

(30) Foreign Application Priority Data
Nov. 3, 2021    (KR) .................. 10-2021-0149745

(51) Int. Cl.
| | |
|---|---|
| *B01J 37/08* | (2006.01) |
| *C07C 29/48* | (2006.01) |
| *B01J 35/00* | (2006.01) |
| *B01J 31/16* | (2006.01) |
| B82Y 30/00 | (2011.01) |
| *B01J 35/10* | (2006.01) |

(52) U.S. Cl.
CPC ......... *B01J 37/084* (2013.01); *B01J 31/1691* (2013.01); *B01J 35/0013* (2013.01); *C07C 29/48* (2013.01); *B01J 35/1023* (2013.01); *B82Y 30/00* (2013.01); *C07C 2531/22* (2013.01)

(58) Field of Classification Search
None
See application file for complete search history.

(56) References Cited

FOREIGN PATENT DOCUMENTS

| | | |
|---|---|---|
| KR | 10-1714574 | 3/2017 |
| KR | 10-1800676 | 11/2017 |
| KR | 10-2021-0075543 | * 6/2021 |
| KR | 1020210075543 | 6/2021 |

OTHER PUBLICATIONS

Lai, Q., et al., "MOF-Based Metal-Doping-Induced Synthesis of Hierarchial Porous Cu-N/C Oxygen Reduction Electrocatalysts for Zn-Air Batteries," Small Journal, 2017, vol. 13, 1700740, pp. 1-11.
Tong, M., et al., "Operando Cooperated Catalytic Mechanism of Atomically Dispersed Cu—N4 and Zn—N4 for Promoting Oxygen Reduction Reaction," Angew. Chem. Int. Ed. 10.1002/anie. 202102053.
Lee, H., et al., "A study on low-temperature methane partial oxidation activity of colloidal ZIF catalyst particles doped with copper ions," 2021 The Korean Society of Industrial and Engineering Chemistry Spring Meeting, May 2021, Abstract.
Jin, W., et al., "Atomic Cu dispersed ZIF-8 derived N-doped carbon for Atomic Cu dispersed ZIF-8 derived N-doped carbon for," J. Phys. Mater., 2021, 4, 024006.
Lee, H. et al., "ZIF-Derived Single-Atom Copper Catalyst on Amorphous Carbon Support for Partial Oxidation of Methane with Enhanced Methanol Selectivity," Nov. 26, 2022, Available at SSRN: https://ssrn.com/abstract=4286826 or http://dx.doi.org/10.2139/ssrn. 4286826.

* cited by examiner

*Primary Examiner* — Yun Qian
(74) *Attorney, Agent, or Firm* — DUANE MORRIS LLP; Gregory M. Lefkowitz

(57) ABSTRACT

A nanocatalyst for partial oxidation of methane is disclosed. The nanocatalyst is prepared by carbonizing a metal-organic framework coordinated with copper ions to form a structure in which nitrogen atoms present in a nitrogen-doped porous carbon structure form coordinate bonds with copper ions. This structure enhances the chemical stability of the nanocatalyst, prevents the peroxidation of methane at low temperature, and significantly improves the conversion efficiency of methane to liquid products such as methanol and methyl hydroperoxide by selective partial oxidation of methane gas. Also disclosed are a method for preparing the nanocatalyst and a method for partial oxidation of methane using the nanocatalyst.

11 Claims, 12 Drawing Sheets

$H_2O_2$ concentration (M)

NANOCATALYST FOR PARTIAL OXIDATION OF METHANE, METHOD FOR PREPARING THE NANOCATALYST AND METHOD FOR PARTIAL OXIDATION OF METHANE USING THE NANOCATALYST

CROSS-REFERENCE TO RELATED APPLICATIONS

This application claims priority under 35 U.S.C. § 119 to Korean Patent Application No. 10-2021-0149745 filed on Nov. 3, 2021 in the Korean Intellectual Property Office, the disclosure of which is incorporated herein by reference in its entirety.

BACKGROUND OF THE INVENTION

1. Field of the Invention

The present invention relates to a nanocatalyst for partial oxidation of methane that can catalyze the partial oxidation of methane gas at low temperature to convert the methane to liquid products such as methanol and methyl hydroperoxide with improved efficiency, a method for preparing the nanocatalyst, and a method for partial oxidation of methane using the nanocatalyst.

2. Description of the Related Art

Oil is widely used as an energy source worldwide and has been gradually depleted. Oil prices will keep rising from now on due to political instability in the Middle East, the largest oil producing region in the world. On the other hand, natural gas is predominantly composed of methane gas ($CH_4$) and its reserves are roughly 40% larger than oil reserves. Natural gas is an inexpensive energy source that is abundantly found all over the world.

Despite its usefulness, however, natural gas is difficult to transport and store because of long distances from places where it is produced to those where it is consumed. Since methane, the main component of natural gas, is in a gaseous state at room temperature and has a low boiling point (−162° C.), it occupies a large volume and suffers from limitations in transport and transfer.

In other words, since methane gas is liquefied at −162° C., its cryogenic cooling and compression are required for transport and storage. However, such cooling and compression processes incur very high energy consumption and costs. For these reasons, methane gas is typically released into the atmosphere or burned off during crude oil production. Thus, a considerable amount of methane is wasted, and methane and carbon dioxide emissions contributing to the greenhouse effect make the environment worse.

Partial oxidation of methane gas to petrochemical fuels such as $C_2+$ hydrocarbons and methanol is expected to overcome the disadvantages of methane gas and supply a larger amount of gas, enabling its use in a wide variety of applications.

Conventional catalysts for partial oxidation of methane gas use porous inorganic oxides such as zeolite or metal-organic structures, but they cause considerable peroxidation of methane gas during methane conversion or lose their stability under reaction conditions.

Thus, there is a need for a new approach to convert methane gas, which has been released into the atmosphere or burned off, to liquid products at low temperature to gain a profit while avoiding the problems of peroxidation of methane gas during methane conversion or poor catalyst stability.

PRIOR ART DOCUMENTS

Patent Documents (Patent Document 1) Korean Patent No. 10-1800676

SUMMARY OF THE INVENTION

The present invention has been made in an effort to solve the above-described problems and one object of the present invention is to provide a nanocatalyst for partial oxidation of methane that is highly chemically stable and catalyzes the partial oxidation of methane at low temperature to convert the methane to liquid products with improved efficiency.

A further object of the present invention is to provide a system including a nanocatalyst for partial oxidation of methane.

Another object of the present invention is to provide a method for partial oxidation of methane.

Still another object of the present invention is to provide a method for preparing a nanocatalyst for partial oxidation of methane.

The present invention provides a nanocatalyst for partial oxidation of methane including a nitrogen-doped porous carbon structure and copper ions coordinated to nitrogen atoms present in the porous carbon structure wherein the porous carbon structure is formed by carbonizing a Zn-based zeolitic imidazole framework (ZIF).

The present invention also provides a system for partial oxidation of methane including the nanocatalyst for partial oxidation of methane.

The present invention also provides a method for partial oxidation of methane, including: adding the nanocatalyst for partial oxidation of methane to water and dispersing the mixture by sonication to prepare a dispersion; and adding an oxidizing agent and methane gas to the dispersion and allowing the reaction for partial oxidation of the methane gas to proceed to form liquid products.

The present invention also provides a method for preparing a nanocatalyst for partial oxidation of methane, including: mixing a copper precursor and a zinc precursor in a first organic solvent to prepare a first mixed solution and mixing an organic precursor with a second organic solvent to prepare a second mixed solution; mixing the first mixed solution with the second mixed solution to prepare a metal-organic framework coordinated with copper ions; carbonizing the metal-organic framework coordinated with copper ions; and treating the carbonized metal-organic framework with an aqueous sulfuric acid solution.

The nanocatalyst for partial oxidation of methane according to the present invention is prepared by carbonizing a metal-organic framework coordinated with copper ions to form a structure in which nitrogen atoms present in a nitrogen-doped porous carbon structure form coordinate bonds with copper ions. This structure enhances the chemical stability of the nanocatalyst, minimizes and prevents the peroxidation of methane at a low temperature of 40° C. or less, and significantly improves the conversion efficiency of methane to liquid products such as methanol and methyl hydroperoxide by selective partial oxidation of methane gas.

Effects of the present invention are not limited to the above-mentioned ones. It should be understood that the effects of the present invention include all effects inferable from the following detailed description.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
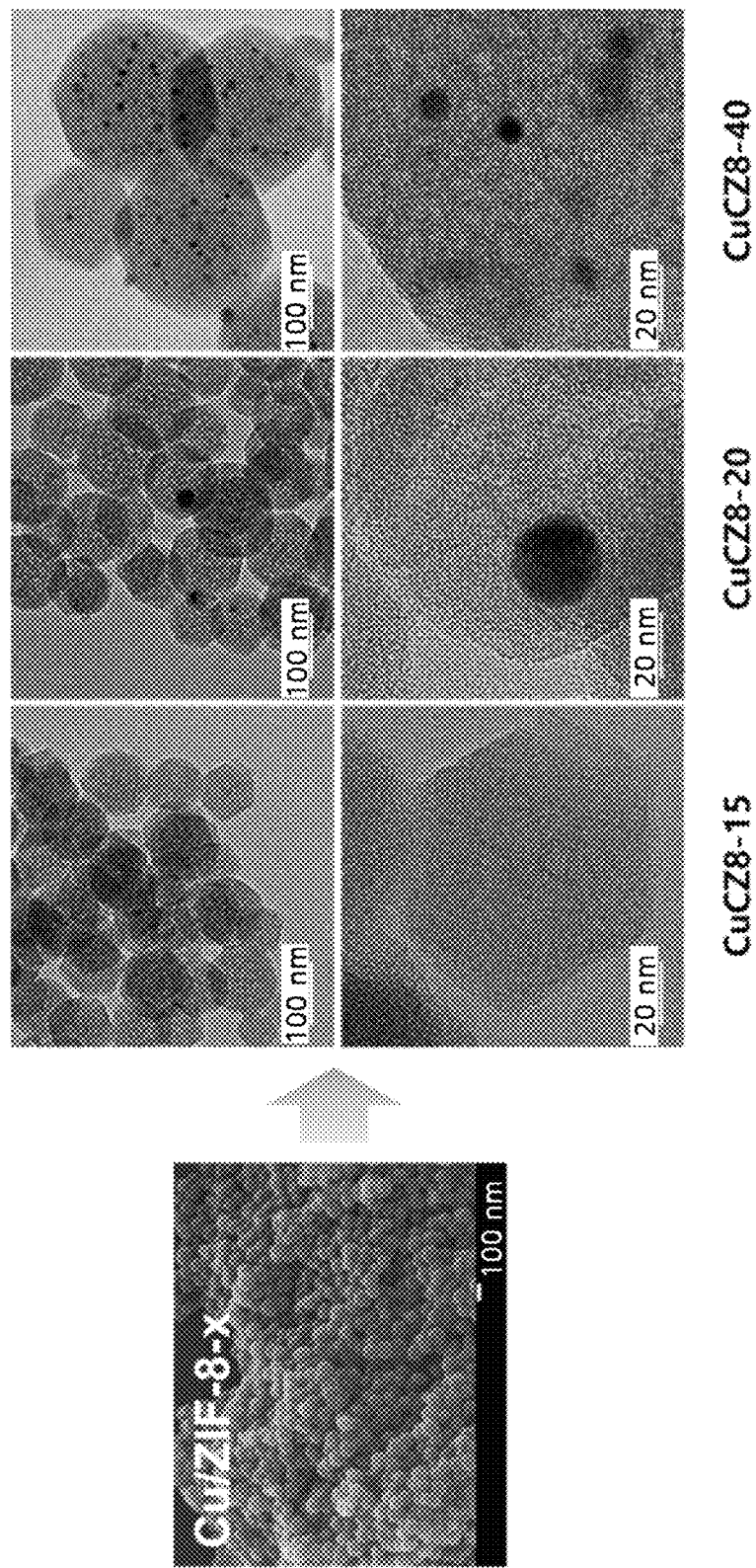
FIG. 1 shows SEM (top) and TEM images (bottom) of nanocatalysts prepared in Examples 3 to 5.

The present invention will now be described in more detail by way of one embodiment.

The present invention is directed to a nanocatalyst for partial oxidation of methane that can catalyze the partial oxidation of methane gas at low temperature to convert the methane to liquid products such as methanol and methyl hydroperoxide with improved efficiency, a method for preparing the nanocatalyst, and a method for partial oxidation of methane using the nanocatalyst.

As described above, conventional catalysts for partial oxidation of methane are prepared by coordinating copper ions to a porous inorganic oxide or metal-organic structure and have the problems of severe peroxidation of methane gas or poor stability. Another problem is that the metal-organic structure is vulnerable to factors such as pH and temperature.

In contrast, the nanocatalyst of the present invention is prepared by carbonizing a metal-organic framework coordinated with copper ions to form a structure in which nitrogen atoms present in a nitrogen-doped porous carbon structure form coordinate bonds with copper ions. This structure enhances the chemical stability of the nanocatalyst, minimizes and prevents peroxidation of methane gas to formic acid at a low temperature of 40° C. or less, and significantly improves the conversion efficiency of methane to liquid products such as methanol and methyl hydroperoxide by selective partial oxidation of methane gas.

Specifically, the present invention provides a nanocatalyst for partial oxidation of methane including a nitrogen-doped porous carbon structure and copper ions coordinated to nitrogen atoms present in the porous carbon structure wherein the porous carbon structure is formed by carbonizing a Zn-based zeolitic imidazole framework (ZIF).

The carbonization induces dehydrogenation, polymerization, etc. to form an organically linked compound. The resulting nitrogen-doped porous carbon structure improves the stability of the catalyst, ensures good physical durability, high chemical stability, and large specific surface area of the catalyst, and increases the amount of copper ions coordinated to nitrogen atoms present therein, achieving improved catalytic activity, compared to conventional metal-organic frameworks.

Specifically, the Zn-based zeolitic imidazole framework (ZIF) may be selected from the group consisting of ZIF-7, ZIF-8, ZIF-22, ZIF-90, ZIF-8-90, ZIF-7-8, and combinations thereof. The Zn-based zeolitic imidazole framework (ZIF) is preferably selected from the group consisting of ZIF-7, ZIF-8, ZIF-22, and combinations thereof. ZIF-8 is most preferred.

The carbonization is performed under an inert gas atmosphere at 850 to 1100° C. for 1 to 5 hours, preferably at 870 to 1000° C. for 1.2 to 3.6 hours, most preferably at 890 to 910° C. for 1.5 to 2.5 hours. If the carbonization temperature is lower than 850° C. or the carbonization time is shorter than 1 hour, a large amount of zinc ions may remain, impeding the conversion of methane gas to methanol as a liquid product. Meanwhile, if the carbonization temperature exceeds 1000° C. or carbonization time exceeds 5 hours, excessive carbonization may occur and the copper ions may be reduced to copper nanoparticles. The excessive carbonization leads to deterioration of the porous carbon structure, resulting in partial loss of the porous carbon structure. The reduction of the copper ions leads to a low conversion yield of methane.

The inert gas may be selected from the group consisting of argon, nitrogen, helium, neon, xenon, krypton, and mixtures thereof. The inert gas is preferably nitrogen.

The copper ions coordinated to nitrogen atoms present in the nitrogen-doped porous carbon structure serve to oxidize methane. The molar proportion of the copper ions in the nanocatalyst for partial oxidation of methane is 17 to 45 mol %, preferably 18 to 40 mol %, more preferably 19 to 30 mol %, most preferably 19 to 22 mol %, as calculated by [copper ions ($Cu^{2+}$)/(copper ions ($Cu^{2+}$)+zinc ions ($Zn^{2+}$))]×100. At this time, if the molar proportion of the copper ions is less than 17 mol %, methane gas may be peroxidized, failing to reach an expected level of conversion efficiency of methane. Meanwhile, if the molar proportion of the copper ions exceeds 45 mol %, the stability of the nanocatalyst may deteriorate, resulting in low conversion of methane.

The nanocatalyst for partial oxidation of methane may be in the form of nanoparticles with an average particle size of 50 to 150 nm, preferably 60 to 140 nm, more preferably 70 to 120 nm, most preferably 80 to 100 nm. If the average particle diameter of the nanocatalyst is less than 50 nm, the catalyst may be difficult to recover. Meanwhile, if the average particle diameter of the nanocatalyst exceeds 150 nm, the decreased specific surface area may lead to a reduction in reactivity.

The nanocatalyst for partial oxidation of methane may have a pore size in the range of 0.4 to 1.1 nm and a specific surface area (BET) in the range of 780 to 910 m$^2$/g. When the pore size and specific surface area of the nanocatalyst are in the respective ranges, the nanocatalyst can effectively transfer methane and has high reactivity.

EXAFS spectroscopy of the nanocatalyst for partial oxidation of methane reveals that peaks corresponding to Cu—N(P1) and Cu—Cu(P2) appear at interatomic distances of 1.4 to 2.0 Å and 2.2 to 2.6 Å, respectively, and the ratio (P1/P2) of the intensity of the Cu—Cu peak (P2) to the intensity of the Cu—N peak (P1) is 0.3-1.4:1, preferably 0.6-1.3:1, most preferably 1.0-1.2:1. The higher the intensity ratio (P1/P2), the larger the proportion of Cu—N bonds in the overall Cu coordination structure.

It is most preferable that the nanocatalyst for partial oxidation of methane satisfies the following conditions: (i) the nanocatalyst is in the form of nanoparticles with an average particle size of 80 to 100 nm; (ii) the nanocatalyst has a pore size of 0.4 to 1.1 nm; (iii) the nanocatalyst has a specific surface area (BET) of 780 to 910 m$^2$/g; (iv) EXAFS spectroscopy of the nanocatalyst reveals that peaks corresponding to Cu—N(P1) and Cu—Cu(P2) appear at interatomic distances of 1.4 to 2.0 Å and 2.2 to 2.6 Å, respectively; and (v) the ratio (P1/P2) of the intensity of the Cu—Cu peak (P2) to the intensity of the Cu—N peak (P1) is 1.0-1.2:1.

Surprisingly, when all of these five conditions are satisfied, the degree of peroxidation of methane to formic acid is constantly minimized or prevented even if the methane conversion temperature is changed or adjusted within the range of 30 to 70° C. However, if any one of the above five conditions is not satisfied, the degree of peroxidation of methane to formic acid may fluctuate drastically when the methane conversion temperature is changed or adjusted within the range of 30 to 70° C.

As demonstrated through numerous experiments and many trials and errors, all of the above five physical properties are achieved only when the carbonization is performed under an inert gas atmosphere at 890 to 910° C. for 1.5 to 2.5 hours and the raw materials are added in such amounts that the molar proportion of copper ions in the nanocatalyst for partial oxidation of methane is 19 to 22 mol %, as calculated by [copper ions (Cu$^{2+}$)/(copper ions (Cu$^{2+}$)+zinc ions (Zn$^{2+}$))]×100.

If either of both conditions is not satisfied, one or more of the above five physical properties may not be achieved, with the result that the degree of peroxidation of methane to formic acid fluctuates drastically when the methane conversion temperature is changed or adjusted within the range of 30 to 70° C.

However, the present invention is not limited to these preparation conditions. Other preparation conditions may also be applicable as long as the above five physical properties are achieved so that the degree of peroxidation of methane to formic acid can be constantly minimized or prevented even if the methane conversion temperature is changed or adjusted within the range of 30 to 70° C., and therefore, it is obvious that they are within the scope of the present invention.

The nanocatalyst for partial oxidation of methane has a structure in which nitrogen atoms present in the nitrogen-doped porous carbon structure form coordinate bonds with copper ions. Due to this structure, the nanocatalyst can activate hydrogen peroxide to form a highly reactive intermediate that can attack C—H bonds, thus being effective for partial oxidation of methane.

Particularly, although not explicitly described in the Examples section that follows, methane conversion yields were measured in the presence of the nanocatalyst for partial oxidation of methane with varying pH values (pH 4, 7, and 10) and temperatures (30, 40, 50, and 70° C.) in the same manner as in Experimental Example 4. As a result, the nanocatalyst was found to have activity for methane conversion without being denatured despite the changes in pH and temperature. These results indicate that the nanocatalyst for partial oxidation of methane according to the present invention is imparted with good acid stability by sulfuric acid treatment after carbonization and is present in a carbonized state, ensuring good chemical stability despite changes in pH and temperature.

The present invention also provides a system for partial oxidation of methane including the nanocatalyst for partial oxidation of methane.

The present invention also provides a method for partial oxidation of methane, including: adding the nanocatalyst for partial oxidation of methane to water and dispersing the mixture by sonication to prepare a dispersion; and adding an oxidizing agent and methane gas to the dispersion and allowing the reaction for partial oxidation of the methane gas to proceed to form liquid products.

The oxidizing agent may be mixed with the nanocatalyst to partially oxidize methane gas. Specifically, the oxidizing agent may be selected from the group consisting of hydrogen peroxide, sulfuric acid, nitric acid, iodic acid, tert-butylhydroxide, and mixtures thereof. The oxidizing agent is preferably hydrogen peroxide.

The oxidizing agent is added at a concentration of 0.1 to 4 M, preferably 0.3 to 2 M, most preferably 0.5 to 1 M, relative to 5 mg of the nanocatalyst for partial oxidation of methane. If the concentration of the oxidizing agent is less than 0.1 M, a high methane conversion yield may not be obtained. Meanwhile, if the concentration of the oxidizing agent exceeds 4 M, the selectivity for methanol may be drastically reduced.

The methane gas may be added at a pressure of 10 to 50 bar, preferably 20 to 40 bar, more preferably 25 to 35 bar, and the reaction for partial oxidation of the methane gas to liquid products may be carried out at 25 to 45° C., preferably 30 to 40° C., more preferably 38 to 40° C., for 10 minutes to 4 hours, preferably 20 minutes to 2 hours, more 25 to 40 minutes.

Particularly, if the reaction temperature is lower than 25° C. or the reaction time is shorter than 10 minutes, the conversion yield of the methane to the liquid products may be greatly reduced. Meanwhile, if the reaction temperature is higher than 45° C. or the reaction time is longer than 4 hours, the methane gas may be peroxidized to formic acid (HCOOH).

The liquid products may be formed when the reaction temperature is 45° C. or less. Specific examples of the liquid products include methanol (CH$_3$OH) and methyl hydroperoxide (CH$_3$OOH). Preferably, methanol is formed as the sole liquid product. If the reaction temperature exceeds 45° C., the methane gas may be peroxidized to form a large amount of formic acid. The selectivity for methanol among the liquid products (CH$_3$OH/(CH$_3$OH+CH$_3$OOH)) is 0.1 to 0.5, preferably 0.2 to 0.45, most preferably 0.3 to 0.4.

The present invention also provides a method for preparing a nanocatalyst for partial oxidation of methane, including: mixing a copper precursor and a zinc precursor in a first organic solvent to prepare a first mixed solution and mixing an organic precursor with a second organic solvent to prepare a second mixed solution; mixing the first mixed solution with the second mixed solution to prepare a metal-organic framework coordinated with copper ions; carbonizing the metal-organic framework coordinated with copper ions; and treating the carbonized metal-organic framework with an aqueous sulfuric acid solution.

The first organic solvent and the second organic solvent may be the same as or different from each other and may be each independently selected from the group consisting of methanol, ethanol, diethylformamide, dimethylacetamide, dimethylformamide, dimethyl sulfoxide, N-methyl-2-pyrrolidone, isopropanol, and mixtures thereof. Preferably, the first organic solvent and the second organic solvent are each independently selected from the group consisting of methanol, ethanol, isopropanol, and mixtures thereof. Each of the first organic solvent and the second organic solvent is most preferably methanol.

The copper precursor may be selected from the group consisting of copper(II) nitrate trihydrate ($Cu(NO_3)_2 \cdot 3H_2O$), copper(II) chloride tetrahydrate ($CuCl_2 \cdot 4H_2O$), copper acetyl acetate, copper sulfate, copper chloride, copper carbonate, copper bromide, copper fluoride, and mixtures thereof. The copper precursor is preferably selected from the group consisting of copper(II) nitrate trihydrate ($Cu(NO_3)_2 \cdot 3H_2O$), copper(II) chloride tetrahydrate ($CuCl_2 \cdot 4H_2O$), copper acetyl acetate, and mixtures thereof. The copper precursor is most preferably copper(II) nitrate trihydrate ($Cu(NO_3)_2 \cdot 3H_2O$).

The zinc precursor may be selected from the group consisting of zinc nitrate hexahydrate ($Zn(NO_3)_2 \cdot 6H_2O$), zinc chloride ($ZnCl_2$), zinc sulfate ($ZnSO_4$), zinc acetate ($Zn(CH_3CO_2)_2$), zinc citrate ($Zn_3[O_2CCH_2C(OH)(CO_2)CH_2CO_2]_2$), zinc nitrate ($Zn(NO_3)_2$), zinc acetate dihydrate ($Zn(OOCCH_3)_2 \cdot 2H_2O$), and mixtures thereof. The zinc precursor is preferably selected from the group consisting of zinc nitrate hexahydrate ($Zn(NO_3)_2 \cdot 6H_2O$), zinc sulfate ($ZnSO_4$), zinc nitrate ($Zn(NO_3)_2$), and mixtures thereof. The zinc precursor is most preferably zinc nitrate hexahydrate ($Zn(NO_3)_2 \cdot 6H_2O$).

The organic precursor may be selected from the group consisting of 2-methylimidazole, imidazole, 1-ethylimidazole, 2-nitroimidazole, 4-methyl-5-imidazolecarboxaldehyde, 5-nitro-1H-benzimidazole, 4-formylimidazole, purin, (1H-imidazol-2-yl)methanol, 5-chlorobenzimidazole, and mixtures thereof. The organic precursor is preferably selected from the group consisting of 2-methylimidazole, imidazole, 1-ethylimidazole, and mixtures thereof. The organic precursor is most preferably 2-methylimidazole.

The first mixed solution may be prepared by mixing the copper precursor and the zinc precursor in a molar ratio of 1:99 to 50:50, preferably 5:95 to 40:60, most preferably 15:85 to 30:70, in the first organic solvent. Particularly, if the molar ratio of the copper precursor to the zinc precursor is <1:99, the activity of the final catalyst may be greatly reduced, which is inefficient. Meanwhile, if the molar ratio of the copper precursor to the zinc precursor is 50:>50, Cu/ZIF-8 nanoparticles may not be formed after the first mixed solution is mixed with the second mixed solution.

The molar proportion of the copper ions in the first mixed solution is 17 to 45 mol %, preferably 18 to 40 mol %, more preferably 19 to 30 mol %, most preferably 19 to 22 mol %, as calculated by [copper ions ($Cu^{2+}$)/(copper ions ($Cu^{2+}$)+ zinc ions ($Zn^{2+}$))]×100.

The metal-organic framework is prepared by mixing the first mixed solution with the second mixed solution in a volume ratio ranging from 40:60 to 60:40, preferably 47:53 to 53:47, most preferably 49:51 to 51:49. If the mixing ratio of the first mixed solution to the second mixed solution is outside the range defined above, the metal-organic framework coordinated with copper ions may not be substantially formed and the particle size may vary.

The step of preparing the metal-organic framework is carried out at room temperature for 30 minutes to 3 hours, preferably 40 minutes to 2 hours, most preferably 50 minutes to 1.2 hours.

The metal-organic framework is carbonized under an inert gas atmosphere at 850 to 1100° C. for 1 to 5 hours, preferably at 870 to 1000° C. for 1.2 to 3.6 hours, most preferably at 890 to 910° C. for 1.5 to 2.5 hours.

The inert gas may be selected from the group consisting of argon, nitrogen, helium, neon, xenon, krypton, and mixtures thereof. The inert gas is preferably nitrogen.

The carbonized metal-organic framework is treated with an aqueous sulfuric acid solution at 70 to 90° C. for 6 to 10 hours, preferably at 75 to 85° C. for 7 to 9 hours, most preferably at 78 to 82° C. for 7.5 to 8.5 hours to completely remove residual zinc ions remaining uncoordinated to and unreacted in the final nanocatalyst for partial oxidation of methane.

The nanocatalyst for partial oxidation of methane may have a structure in which nitrogen atoms present in a nitrogen-doped porous carbon structure form coordinate bonds with copper ions.

The nanocatalyst for partial oxidation of methane has an average particle diameter of 50 to 150 nm, preferably 60 to 140 nm, more preferably 70 to 120 nm, most preferably 80 to 100 nm.

Particularly, although not explicitly described in the Examples section that follows, nanocatalysts for partial oxidation of methane were prepared and methane conversion yields in the presence of the nanocatalysts were measured by varying the following 10 conditions: (1) each of the first organic solvent and the second organic solvent is methanol; (2) the copper precursor is copper(II) nitrate trihydrate ($Cu(NO_3)_2 \cdot 3H_2O$); (3) the zinc precursor is zinc nitrate hexahydrate ($Zn(NO_3)_2 \cdot 6H_2O$); (4) the organic precursor is 2-methylimidazole; (5) the molar proportion of the copper ions in the first mixed solution is 19 to 22 mol %, as calculated by [copper ions ($Cu^{2+}$)/(copper ions ($Cu^{2+}$)+zinc ions ($Zn^{2+}$))]×100; (6) the step of preparing the metal-organic framework coordinated with copper ions is carried out at room temperature for 50 minutes to 1.2 hours; (7) the metal-organic framework is carbonized under an inert gas atmosphere at 890 to 910° C. for 1.5 to 2.5 hours; (8) the carbonized metal-organic framework is treated with an aqueous sulfuric acid solution at 78 to 82° C. for 7.5 to 8.5 hours to remove residual zinc ions in the nanocatalyst for partial oxidation of methane; (9) the nanocatalyst for partial oxidation of methane has a structure in which nitrogen atoms present in a nitrogen-doped porous carbon structure form coordinate bonds with copper ions; and (10) the nanocatalyst for partial oxidation of methane is in the form of nanoparticles with an average particle size of 80 to 100 nm. Each measurement was repeated 100 times.

As a result, despite repeated use (100 times) of each nanocatalyst, the formation of formic acid by peroxidation of methane was not observed. The conversion yields of methane gas to methanol and methyl hydroperoxide as liquid products were as high as 90 µmol/g and >95 µmol/g, respectively.

However, if any one of the above 10 conditions is not met, methane gas was peroxidized to formic acid after 30 times repeated use and the conversion yields of methane gas to methanol and methyl hydroperoxide decreased rapidly to 72 μmol/g and 76 μmol/g, respectively.

The present invention will be more specifically explained with reference to the following examples. However, these examples are not intended to limit the scope of the present invention.

Examples 1 to 5: Preparation of Nanocatalysts for Partial Oxidation of Methane (Cu/CZ8)

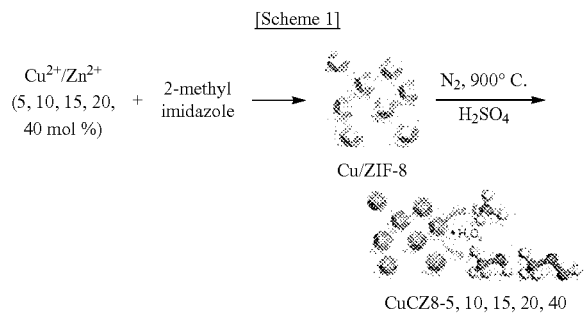

[Scheme 1]

$Cu^{2+}/Zn^{2+}$ (5, 10, 15, 20, 40 mol %) + 2-methyl imidazole → Cu/ZIF-8 → $N_2$, 900° C. / $H_2SO_4$ → CuCZ8-5, 10, 15, 20, 40

$Cu(NO_3)_2 \cdot 3H_2O$ and $Zn(NO_3)_2 \cdot 6H_2O$ (total 13.27 mmol) in the ratio shown in Table 1 were dissolved in 150 mL of methanol to prepare a first mixed solution. 106.2 mmol of 2-methylimidazole was dissolved in 150 mL of methanol to prepare a second mixed solution. Then, the first mixed solution and the second mixed solution were mixed in a 50:50 volume ratio. The mixture was allowed to react at room temperature for 1 h to prepare a metal-organic framework coordinated with copper ions (Cu/ZIF-8). Cu/ZIF-8 was centrifuged, filtered, washed several times with methanol, and dried in an oven at 60° C. for one day.

After drying, Cu/ZIF-8 was carbonized under a nitrogen atmosphere at a temperature of 900° C. (heating rate 2° C./min) for 2 h to prepare a nanocatalyst for partial oxidation of methane (Cu/CZ8-x). After completion of the carbonization, the resulting Cu/CZ8-x powder was dispersed in a 1 N aqueous sulfuric acid solution, stirred at 80° C. for 8 h to remove remaining Zn, and centrifuged to obtain a final nanocatalyst for partial oxidation of methane (CuCZ8-x; x is the molar ratio $Cu^{2+}/(Cu^{2+}+Zn^{2+})$ used to prepare Cu/ZIF-8) as a black powder. CuCZ8-5 (Example 1), CuCZ8-10 (Example 2), CuCZ8-15 (Example 3), CuCZ8-20 (Example 4), and CuCZ8-40 (Example 5) were prepared as shown in Table 1.

determine particle morphologies and constituents of the nanocatalysts. The results are shown in FIGS. 1 and 2.

FIG. 1 shows SEM (top) and TEM images (bottom) of the nanocatalysts prepared in Examples 3-5. Referring to FIG. 1, each of the nanocatalysts was in the form of spherical nanoparticles with an average particle diameter of ~80-100 nm irrespective of the content of copper ions. Each of the nanocatalysts of Examples 4 and 5 had a structure in which copper nanoparticles were formed in the nitrogen-doped porous carbon structure.

Figure 2:
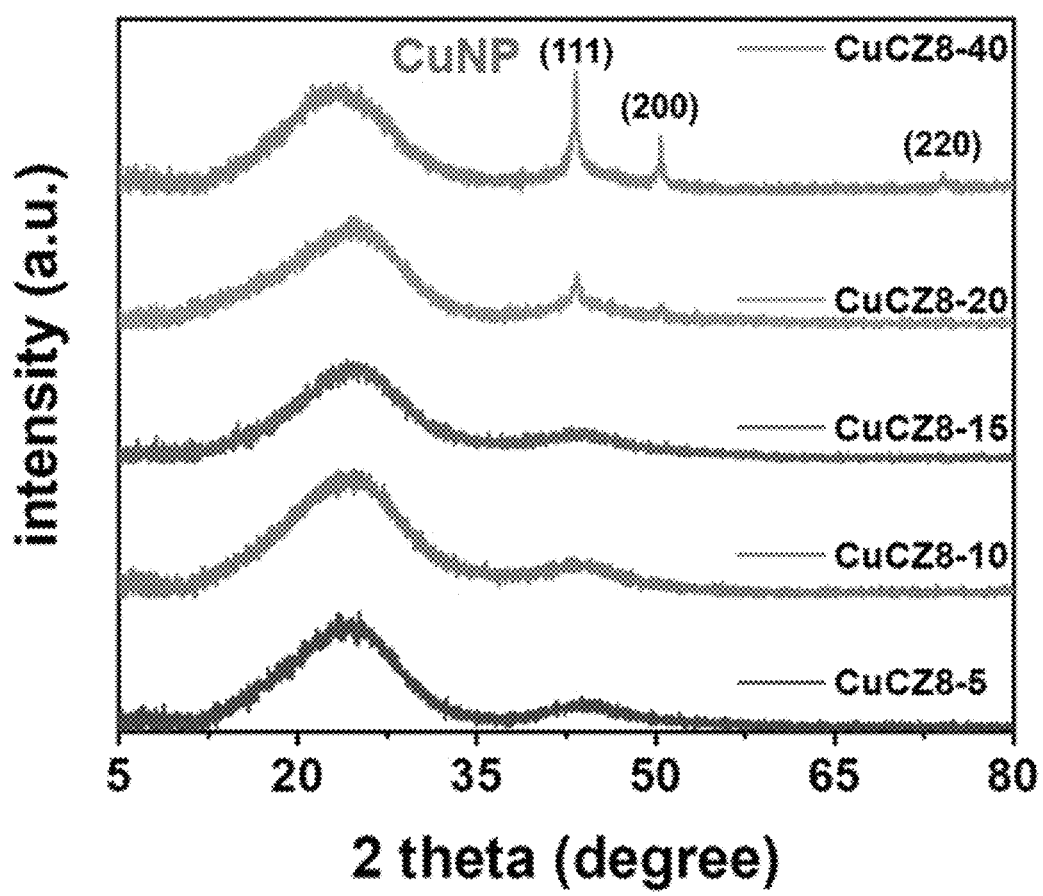
FIG. 2 shows XRD patterns of nanocatalysts prepared in Examples 1 to 5.

FIG. 2 shows XRD patterns of the nanocatalysts prepared in Examples 1-5. Referring to FIG. 2, peaks corresponding to copper nanoparticles were detected in the XRD patterns of the nanocatalysts prepared in Examples 4-5. As for the nanocatalyst of Example 4, the peaks appeared only in specific regions, indicating that 20 mol % represents a critical point for the formation of copper nanoparticles.

In contrast, no peaks corresponding to copper nanoparticles were detected in the XRD patterns of the nanocatalysts prepared in Examples 1-3. That is, only a single-atom copper species was formed when the content of copper ions was 5-15 mol %.

Experimental Example 2: Analysis of XANES and EXAFS Spectra of the Nanocatalysts X-ray absorption near edge structure (XANES) spectra of the nanocatalysts prepared in Examples 1-5 were analyzed using a beamline at the Pohang Accelerator Laboratory and Fourier transform-extended X-ray absorption fine structure (EXAFS) spectra of the nanocatalysts were analyzed to determine the local structures of copper nanoparticles present in the nanocatalysts. The results are shown in FIGS. 3 and 4 and Table 1.

Figure 3A:
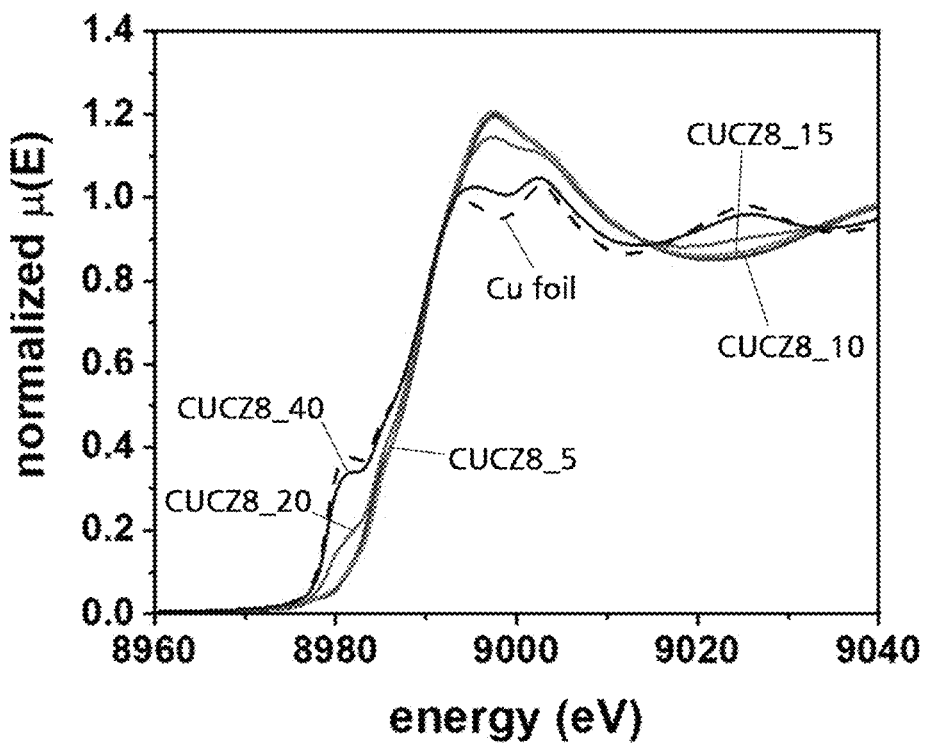
FIGS. 3A and 3B show XANES spectra of nanocatalysts prepared in Examples 1 to 5.
Figure 3B:
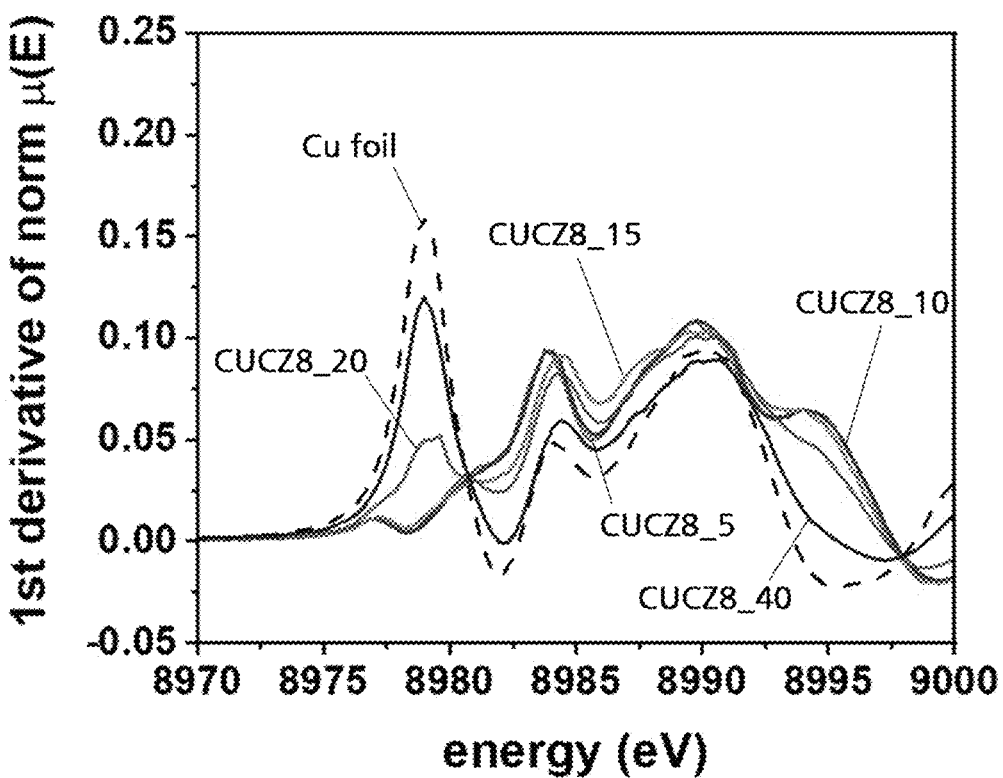
Figure 4A:
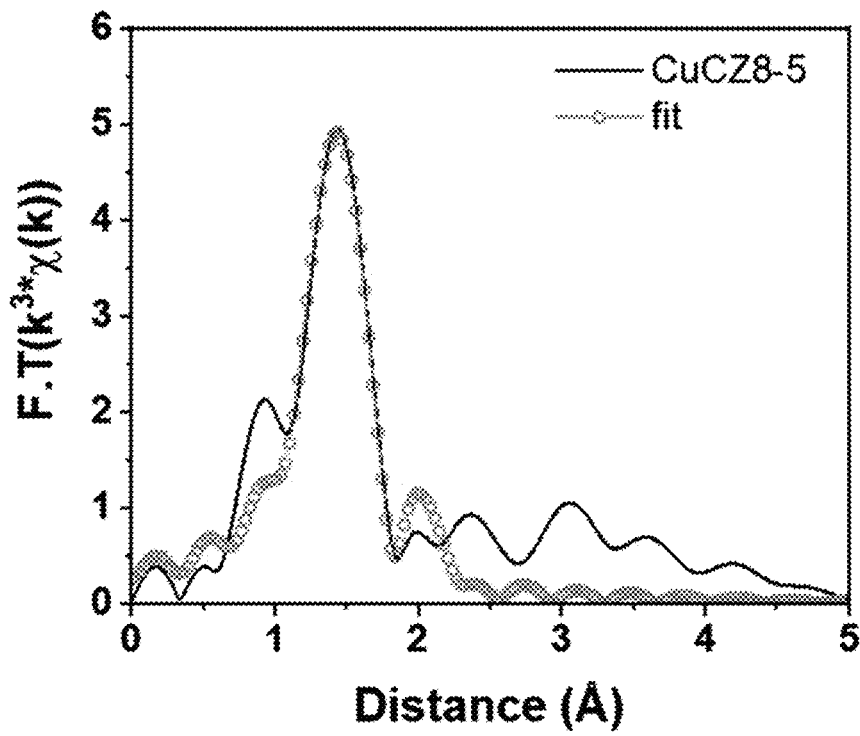
FIGS. 4A to 4E show EXAFS spectra of nanocatalysts prepared in Examples 1 to 5.
Figure 4B:
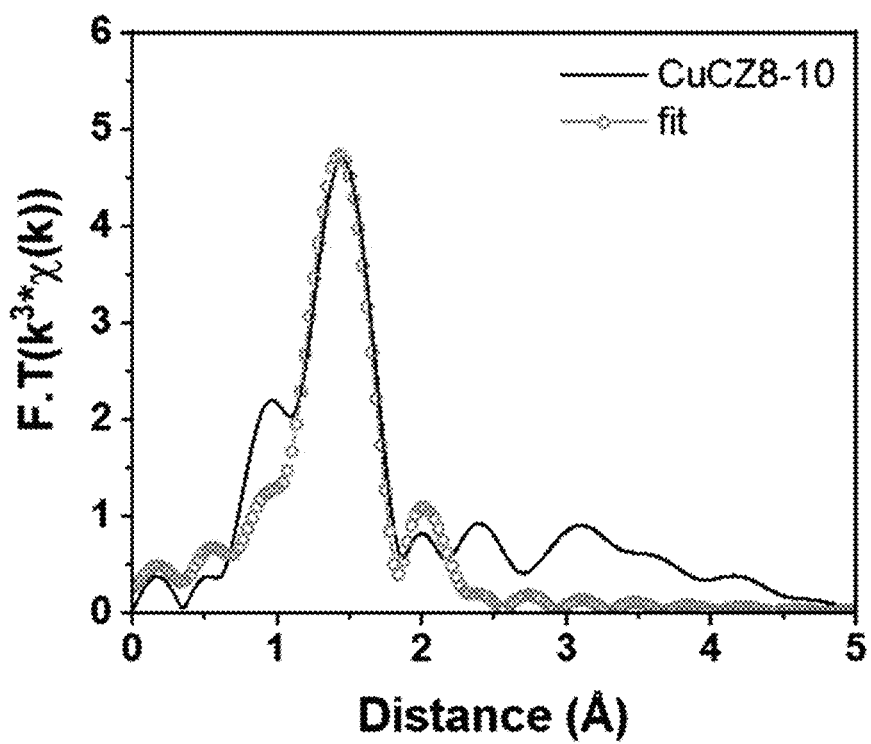
Figure 4C:
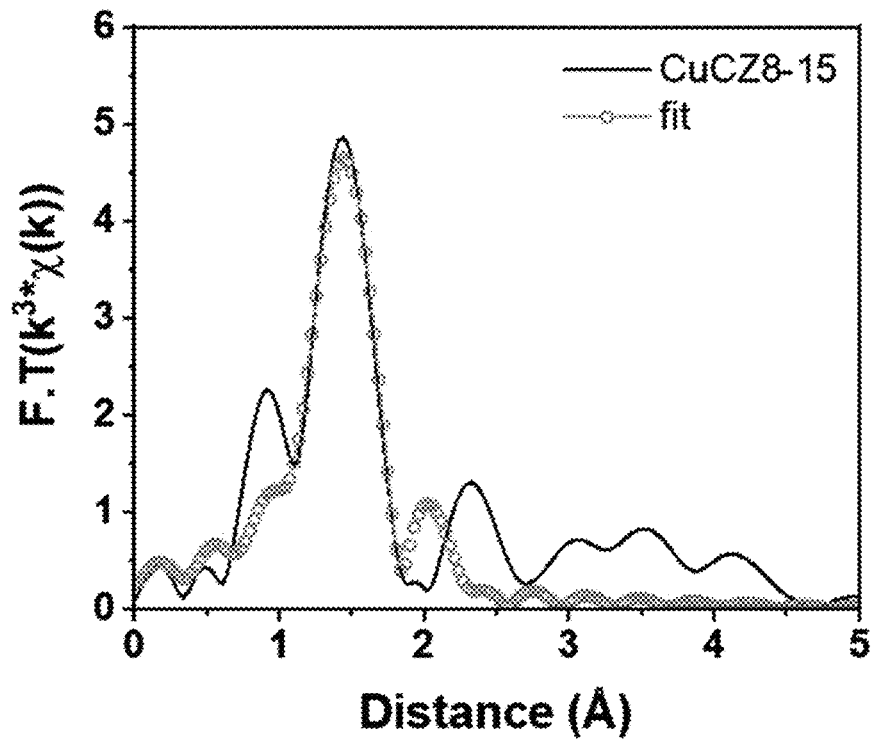
Figure 4D:
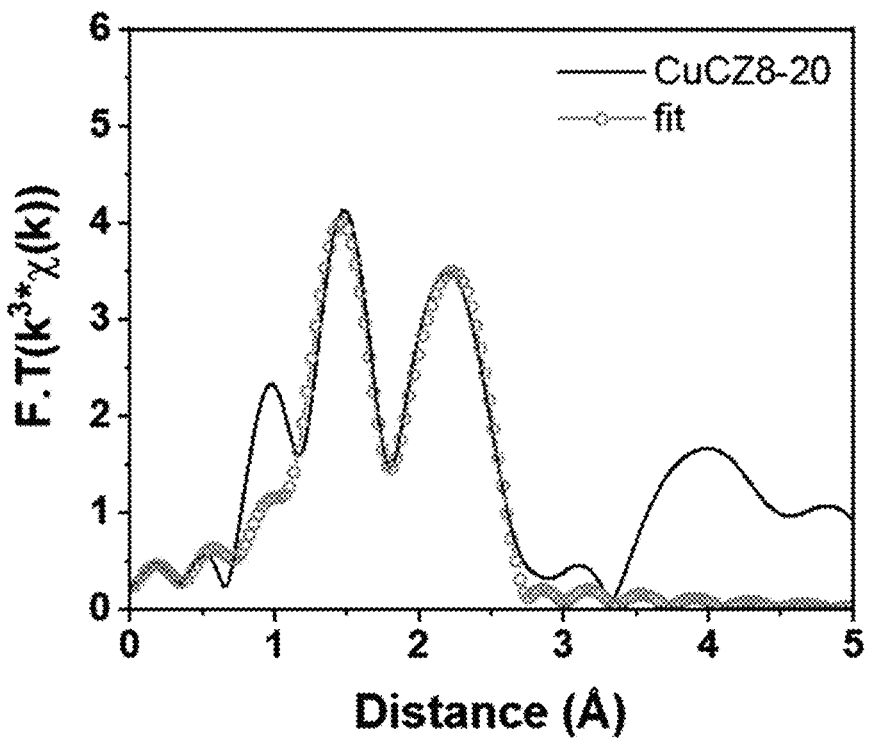
Figure 4E:
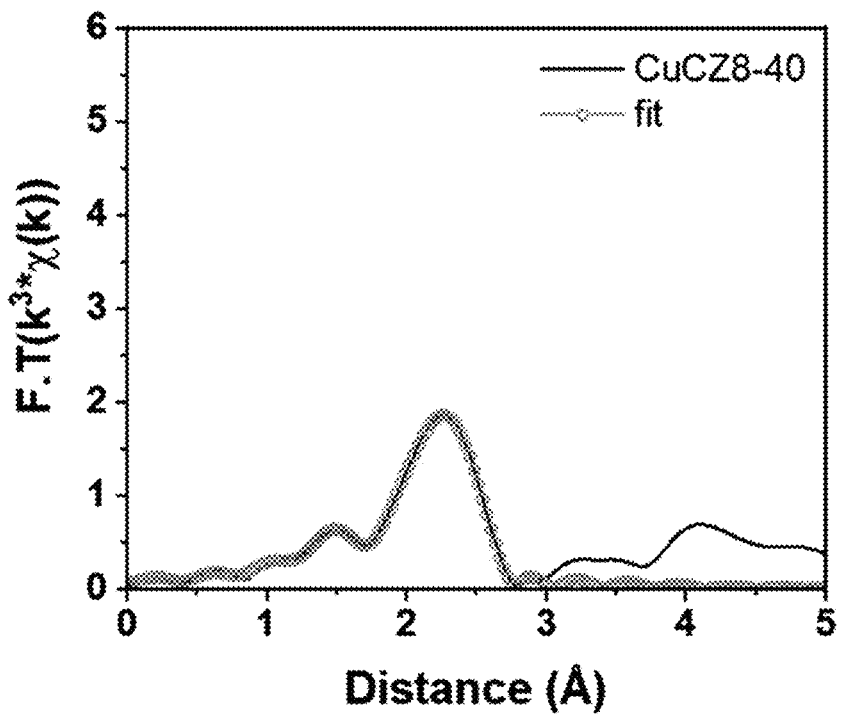

FIG. 3A shows XANES spectra and FIG. 3B shows first-order differential XANES spectra of the nanocatalysts prepared in Examples 1-5. Referring to FIG. 3A, no peaks corresponding to Cu(0) appeared at an energy of 8981 eV in the spectra of the nanocatalysts of Examples 1-3. In contrast, a weak peak corresponding to Cu(0) appeared in the spectrum of the nanocatalyst of Example 4 and a strong peak appeared in the spectrum of the nanocatalyst of Example 5. That is, the greater the molar proportion of copper nanoparticles, the stronger the Cu(0) peak, as revealed in FIGS. 1 and 2.

For more detailed analysis, the spectra were first-order differentiated (FIG. 3B), where the oxidation numbers were analyzed with the chemical shift of the highest peak (K-edge energy). The K-edge energy of Cu(0) appeared as a peak at

TABLE 1

| | $Cu(NO_3)_2 \cdot 3H_2O$ (mmol) | $Zn(NO_3)_2 \cdot 6H_2O$ (mmol) | Molar ratio $[Cu^{2+}/(Cu^{2+}+Zn^{2+})] \times 100$ (mol %) |
|---|---|---|---|
| Example 1 (CuCZ8-5) | 0.66 | 12.61 | 5 |
| Example 2 (CuCZ8-10) | 1.33 | 11.95 | 10 |
| Example 3 (CuCZ8-15) | 1.99 | 11.28 | 15 |
| Example 4 (CuCZ8-20) | 2.65 | 10.62 | 20 |
| Example 5 (CuCZ8-40) | 5.31 | 7.96 | 40 |

Experimental Example 1: Analysis of SEM Images, TEM Images and XRD Patterns of the Nanocatalysts SEM images, TEM images, and XRD patterns of the nanocatalysts prepared in Examples 1-5 were analyzed to 8979 eV, which is the theoretical value, and increased with increasing oxidation number. The main oxidation state of Cu in the nanocatalyst of Example 5 (CuCZ8-40) was Cu(0), which was due to the formation of Cu nanoparticles, as confirmed also in the other XRD patterns. In the spectra of the nanocatalysts of Examples 1-3 (CuCZ8-5,10,15), no peaks appeared at 8979 eV and the highest peak (k-edge energy) appeared at ~8990 eV, indicating that the main oxidation number was +2.

FIGS. 4A to 4E shows EXAFS spectra of the nanocatalysts prepared in Examples 1-5.

Table 2 shows parameters obtained by fitting of Cu—N bonds and Cu—Cu bonds in the nanocatalysts of Examples 1-5.

TABLE 2

| Path | | Coordination number | Distance (Å) | DWF$^a$ (Å$^2$) | $\Delta E_0^b$ (eV) | R-factor$^c$ |
|---|---|---|---|---|---|---|
| Example 1 (CuCZ8-5) | Cu—N | 3.9 | 1.93 | 0.007 | −5.073 | 0.005 |
| Example 2 (CuCZ8-10) | Cu—N | 3.9 | 1.93 | 0.007 | −4.914 | 0.009 |
| Example 3 (CuCZ8-15) | Cu—N | 3.7 | 1.94 | 0.007 | −3.961 | 0.014 |
| Example 4 (CuCZ8-20) | Cu—N | 3.2 | 1.94 | 0.008 | −3.343 | 0.015 |
| | Cu—Cu | 3.0 | 2.55 | 0.012 | | |
| Example 5 (CuCZ8-40) | Cu—N | 1.8 | 1.92 | 0.009 | 5.271 | 0.001 |
| | Cu—Cu | 6.8 | 2.55 | 0.009 | | |

$^a$Debye-Waller factor;
$^b$threshold energy shift;
$^c$a measure of the mean square sum of the misfit at each data point.
Fit range: 2.5 < k < 11 Å$^{-1}$; 1 < R < 3 Å.
Fit window: Hanning Referring to FIGS. 4A to 4E and Table 2, peaks corresponding to CuN$_4$, where one copper ion is coordinated to four nitrogen atoms, appeared at an interatomic distance of ~1.4-2.0 Å in the spectra of the nanocatalysts of Examples 1-3 (CuCZ8-5,10,15). The absence of Cu—Cu bonds indicated the existence of all Cu atoms as single atoms.

In contrast, peaks (P1) corresponding to Cu—N in the form of CuN$_4$, where one copper ion is coordinated to four nitrogen atoms, appeared at an interatomic distance of ~1.4-2.0 Å in the spectra of the nanocatalysts of Examples 4-5 (CuCZ8-20,40). Peaks (P2) corresponding to Cu—Cu bonds appeared in the range of ~2.2-2.6 Å. The formation of copper nanoparticles was responsible for the Cu—Cu bonds. The peak intensity ratio (P1/P2) was ~1.0-1.2 for the nanocatalyst of Example 4 and ~~0.3-0.5 for the nanocatalyst of Example 5. In the nanocatalyst of Example 5 (CuCZ8-40), most of the Cu atoms exist as nanoparticles.

Experimental Example 3: Analysis of Pore Sizes and Specific Surface Areas (BET) of the Nanocatalysts The pore sizes and specific surface areas (BET) of the nanocatalysts prepared in Examples 1-5 were analyzed by suitable methods known in the art. The results are shown in FIG. 5 and Table 3.

Figure 5:
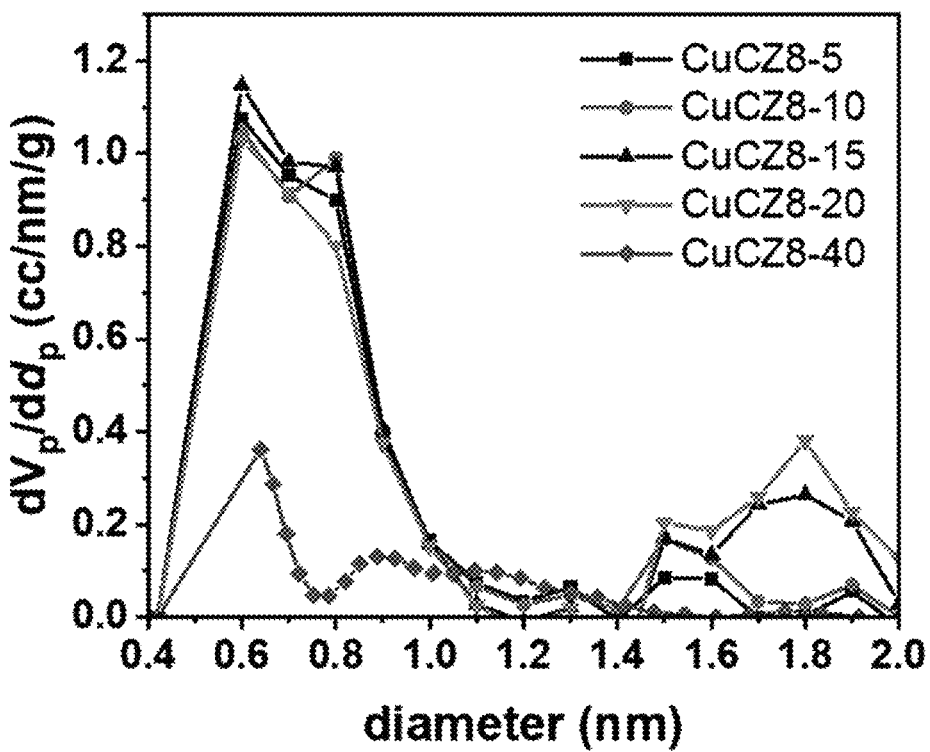
FIG. 5 shows the pore size distributions of nanocatalysts prepared in Examples 1 to 5.

FIG. 5 shows the pore size distributions of the nanocatalysts prepared in Examples 1-5. Referring to FIG. 5, the pore sizes of the nanocatalysts of Examples 1-5 were 0.6-1 nm.

Table 3 shows the specific surface areas (BET) and pore volumes of the nanocatalysts prepared in Examples 1-5.

Referring to Table 3, the pore volumes of the nanocatalysts of Examples 1-3 demonstrated the formation of well-defined micropores and the specific surface areas of the nanocatalysts of Examples 1-3 were close to 1000 m$^2$/g.

In contrast, due to the increased contents of copper ions in the nanocatalysts of Examples 4-5, the microporous structures were destroyed, resulting in an increase in pore size. As a result, the specific surface areas of the nanocatalysts of Examples 4-5 were small but the pore volumes of the nanocatalysts of Examples 4-5 were large compared to those of the nanocatalysts of Examples 1-3.

Experimental Example 4: Analysis of Elemental Contents and N Species Distributions in Nanocatalysts Prepared Through Carbonization at Different Temperatures Nanocatalysts were prepared in the same manner as in Example 4, except that the carbonization temperature was changed to 700° C. (Example 4-1), 800° C. (Example 4-2), 900° C. (Example 4-3), and 1000° C. (Example 4-4). The elemental contents and N species distributions in the nanocatalysts and N$_2$ adsorption-desorption isotherms of the nanocatalysts were analyzed as a function of copper ion content or carbonization temperature. The results are shown in FIGS. 6 and 7 and Tables 4 and 5.

Figure 6:
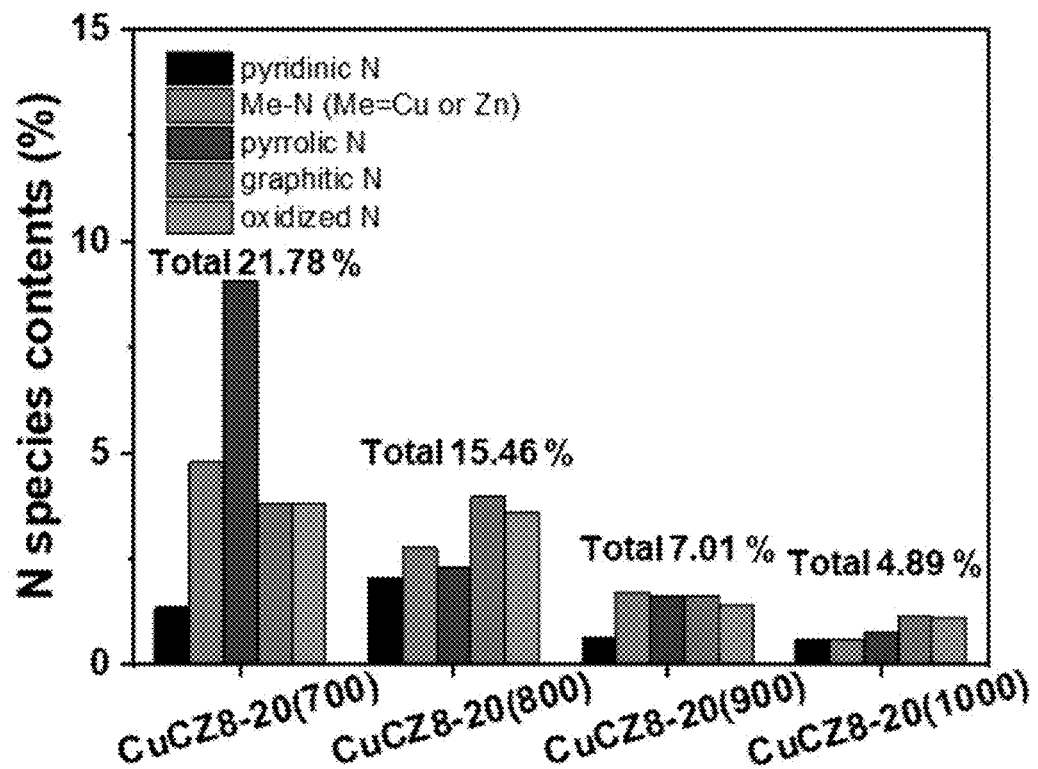
FIG. 6 shows XPS Nis data for nanocatalysts prepared through carbonization at different temperatures in Example 4.

FIG. 6 shows XPS N1s data for the nanocatalysts prepared through carbonization at different temperatures in Example 4. Referring to FIG. 6, each of the nanocatalysts was composed of pyridinic N, Me-nitrogen (Me=copper or zinc), pyrrolic N, graphitic nitrogen, and oxidized N. Particularly, the contents of Me-nitrogen, where nitrogen was coordinated with copper ions or zinc ions, were less than 5 wt %. Among them, the contents of Me-nitrogen in the nanocatalysts prepared through carbonization at 900° C. and 1000° C. were reduced to less than 2.5 wt % due to the formation of copper nanoparticles.

Figure 7:
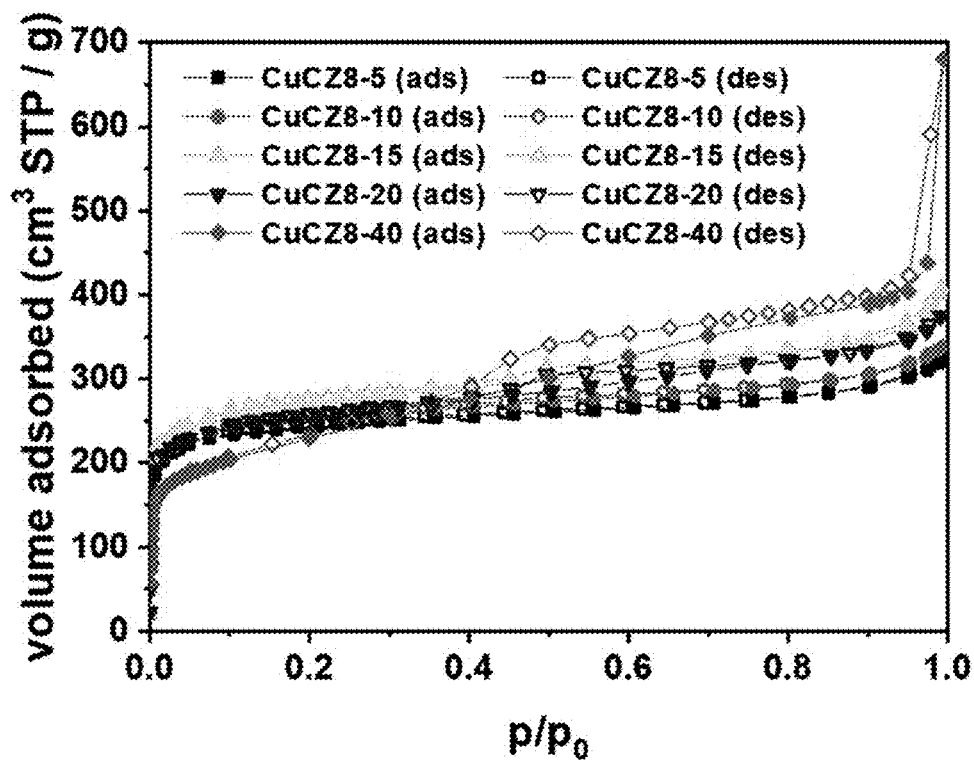
FIG. 7 shows $N_2$ adsorption-desorption isotherms of nanocatalysts prepared in Examples 1 to 5.

FIG. 7 shows N$_2$ adsorption-desorption isotherms of the nanocatalysts prepared in Examples 1-5. Referring to FIG. 7, the nanocatalysts of Examples 1-2 had type 1 isotherms, indicating that N$_2$ molecules were adsorbed in the form of a monomolecular layer to the pores and the pore sizes were rather constant. Hysteresis loops were observed the nanocatalysts of Examples 3-5 due to capillary condensation, indicating the formation of mesopores with a size of 2-100 nm. Particularly, many hollows were formed in the nanocatalyst of Example 5.

Tables 4 and 5 show the contents (%) of the elements of the nanocatalysts prepared in Examples 1, 2, 4 and 5.

TABLE 4

| | Atomic % | | | |
|---|---|---|---|---|
| Element | Example 1 (CuCZ8-5) | Example 2 (CuCZ8-10) | Example 4 (CuCZ8-20) | Example 5 (CuCZ8-40) |
| C | 83.97 | 83.42 | 83.49 | 85.25 |
| O | 7.97 | 8.06 | 8.95 | 7.28 |

TABLE 3

| | Example 1 (CuCZ8-5) | Example 2 (CuCZ8-10) | Example 3 (CuCZ8-15) | Example 4 (CuCZ8-20) | Example 5 (CuCZ8-40) |
|---|---|---|---|---|---|
| BET surface area (m$^2$/g) | 929 | 1062 | 1035 | 796 | 823 |
| Pore volume (cc/g) | 0.50 | 0.52 | 0.62 | 0.58 | 1.053 |

TABLE 4-continued

| | Atomic % | | | |
|---|---|---|---|---|
| Element | Example 1 (CuCZ8-5) | Example 2 (CuCZ8-10) | Example 4 (CuCZ8-20) | Example 5 (CuCZ8-40) |
| N | 7.44 | 7.85 | 7.01 | 6.92 |
| Cu | 0.16 | 0.25 | 0.30 | 0.33 |
| Zn | 0.45 | 0.42 | 0.26 | 0.21 |
| Total | 99.99 | 100 | 100.01 | 100 |

As can be seen from the results in Table 4, as the content of copper ions increased from the nanocatalyst of Example 1 to the nanocatalyst of Example 5, the content of zinc ions was reduced because zinc ions to prepare Cu/ZIF-8 was reduced. Carbon (C), oxygen (O), and nitrogen (N) were maintained at the same levels without changes in their contents.

TABLE 5

| | Atomic % | | | |
|---|---|---|---|---|
| Element | Example 4-1 (CuCZ8-20_700) | Example 4-2 (CuCZ8-20_800) | Example 4-3 (CuCZ8-20_900) | Example 4-4 (CuCZ8-20_1000) |
| C | 69.43 | 75.08 | 83.49 | 87.92 |
| O | 7.57 | 8.27 | 8.95 | 6.93 |
| N | 21.78 | 15.46 | 7.01 | 4.89 |
| Cu | 0.13 | 0.32 | 0.30 | 0.26 |
| Zn | 1.09 | 0.86 | 0.26 | 0 |
| Total | 100 | 99.99 | 100.01 | 100 |

As can be seen from the results in Table 5, as the carbonization temperature increased, the carbon content increased, the nitrogen and zinc contents decreased gradually, and the content of copper ions was maintained at a similar level. Particularly, the content of nitrogen atoms was reduced to 7.01 and 4.89 atomic % in the nanocatalysts of Examples 4-3 and 4-4, respectively, and as a result, the numbers of sites capable of being stably coordinated with ionized copper atoms decreased, indicating the formation of nanoparticles due to the aggregation of copper atoms.

Experimental Example 5: Analysis of XRD Patterns and XANES Spectra of Nanocatalysts Prepared Through Carbonization at Different Temperatures Nanocatalysts were prepared in the same manner as in Example 4, except that the carbonization temperature was changed to 700° C. (Example 4-1), 800° C. (Example 4-2), 900° C. (Example 4-3), and 1000° C. (Example 4-4). XRD patterns and XANES spectra of the nanocatalysts were analyzed to determine the local structures of constituents and copper nanoparticles of the nanocatalysts.

Figure 8:
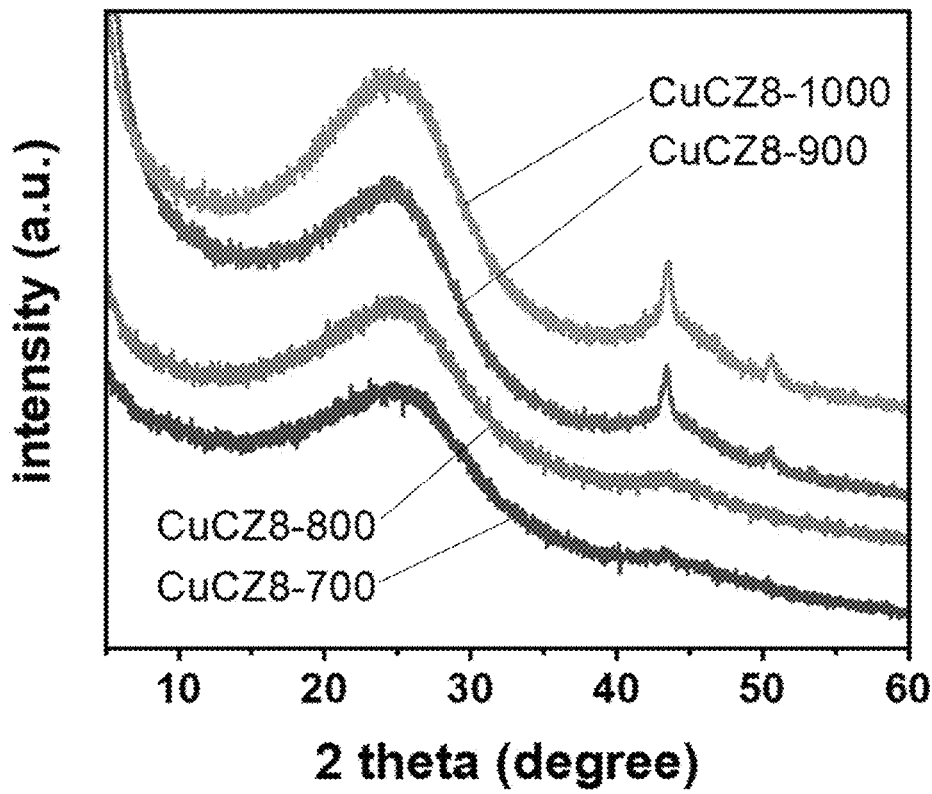
FIG. 8 shows XRD spectra of nanocatalysts prepared through carbonization at different temperatures (700, 800, 900, and 1000° C.) in Example 4.
Figure 9:
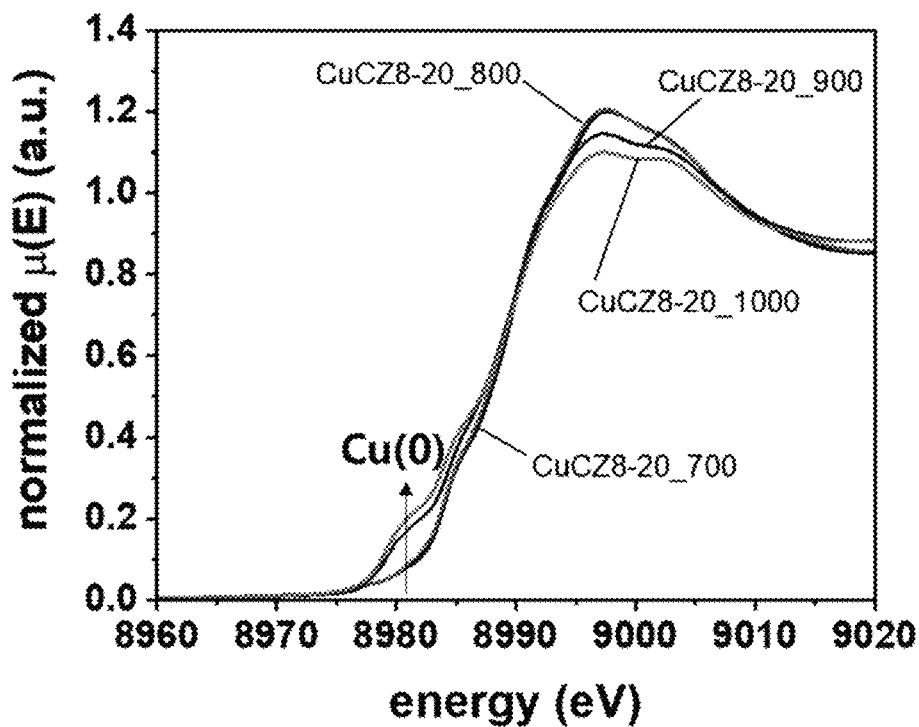
FIG. 9 shows XANES spectra of nanocatalysts prepared through carbonization at different temperatures (700, 800, 900, and 1000° C.) in Example 4.

The results are shown in FIGS. 8 and 9.

FIG. 8 shows XRD spectra of the nanocatalysts prepared through carbonization at different temperatures (700, 800, 900, and 1000° C.) in Example 4.

FIG. 9 shows XANES spectra of the nanocatalysts prepared through carbonization at different temperatures (700, 800, 900, and 1000° C.) in Example 4.

Referring to FIGS. 8 and 9, no peaks corresponding to copper nanoparticles were detected in the spectra of the nanocatalysts prepared through carbonization at temperatures of 700 and 800° C. in Examples 4-1 and 4-2, respectively. In contrast, peaks corresponding to copper nanoparticles were detected in the spectra of the nanocatalysts prepared through carbonization at temperatures of 900 and 1000° C. in Examples 4-3 and 4-4, respectively.

Experimental Example 6: Analysis of Methane Conversion Yields in the Presence of Nanocatalysts Prepared Through Carbonization at Different Temperatures Nanocatalysts were prepared in the same manner as in Example 4, except that the carbonization temperature was changed to 700° C. (Example 4-1), 800° C. (Example 4-2), 900° C. (Example 4-3), and 1000° C. (Example 4-4). The methane conversion yields in the presence of the nanocatalysts were measured. The results are shown in FIG. 10.

Methane was converted by the following procedure. First, 5 mg of each of the nanocatalysts was added to 10 ml of water and dispersed by sonication to prepare a dispersion. Then, the dispersion and 0.5 M hydrogen peroxide as an oxidizing agent were charged into a stainless steel autoclave, and methane gas containing 5% helium was introduced at 28.5 bar-g. Then, the autoclave was placed in a water bath set at a temperature to 40° C. and the reaction was allowed to proceed for 30 min. After completion of the reaction, the autoclave was placed in ice water to cool down. Gas products were analyzed by gas chromatography. Liquid products were centrifuged to recover the catalyst and quantitatively analyzed by nuclear magnetic resonance spectroscopy.

Figure 10:
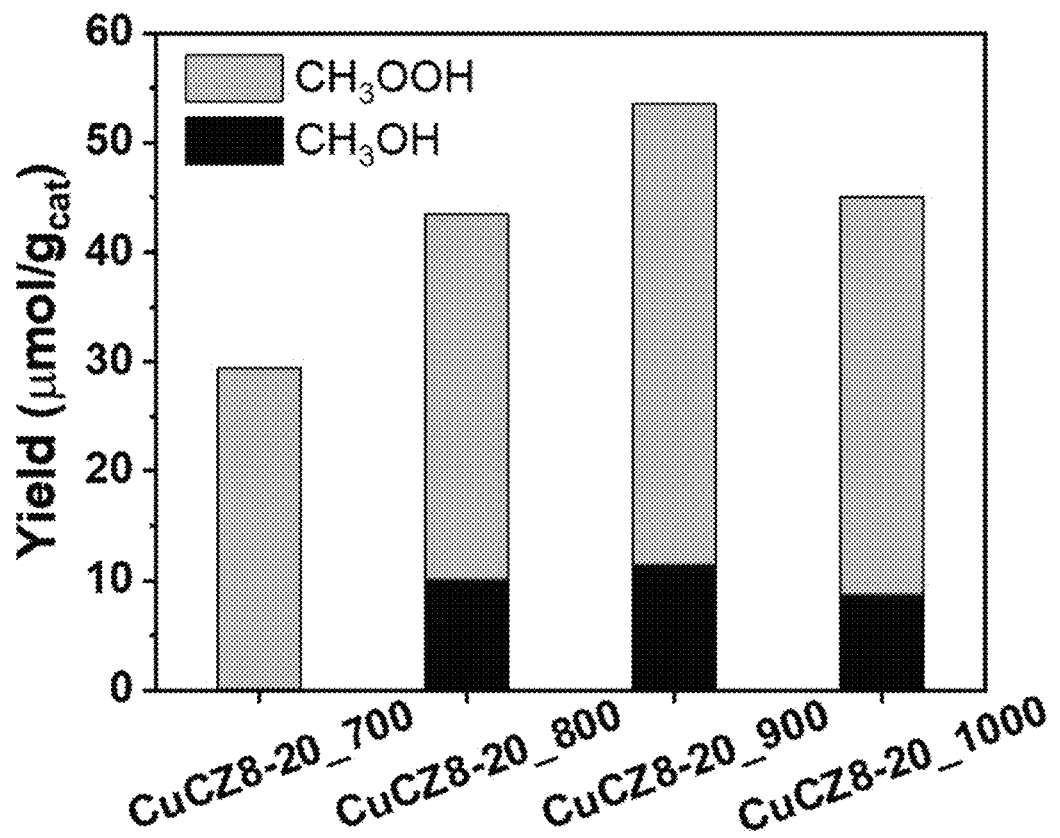
FIG. 10 shows methane conversion yields in the presence of nanocatalysts prepared through carbonization at different temperatures in Example 4.
Figure 11A:
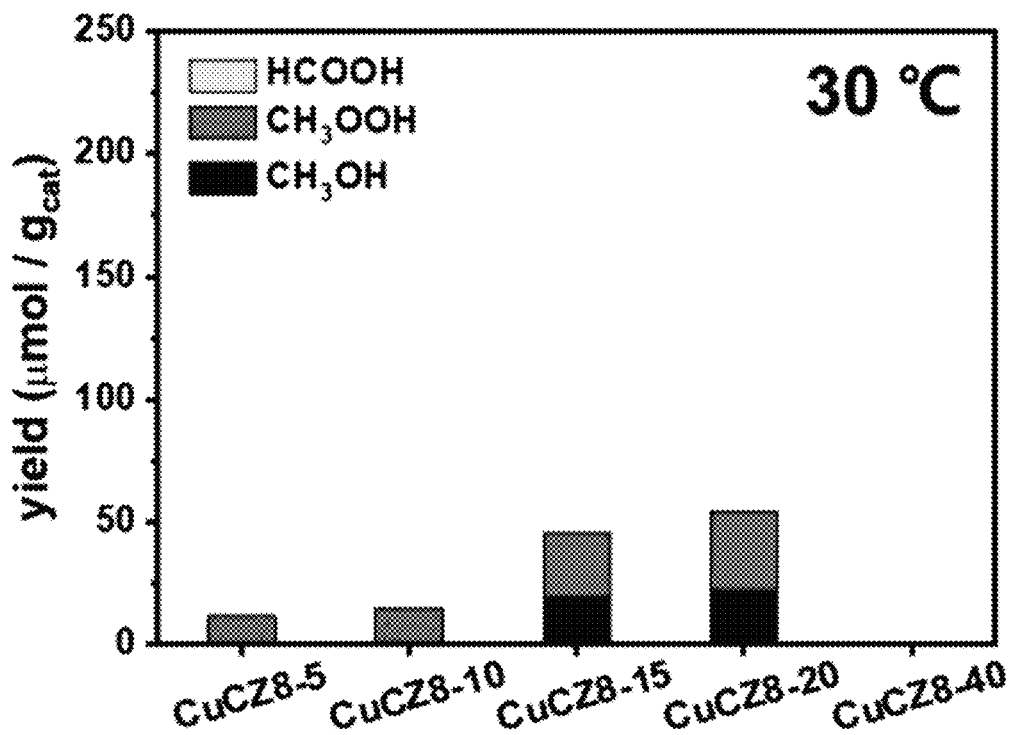
FIGS. 11A to 11D show methane conversion yields at different temperatures (30° C., 40° C., 50° C., and 70° C.) in the presence of nanocatalysts prepared in Examples 1 to 5.
Figure 11B:
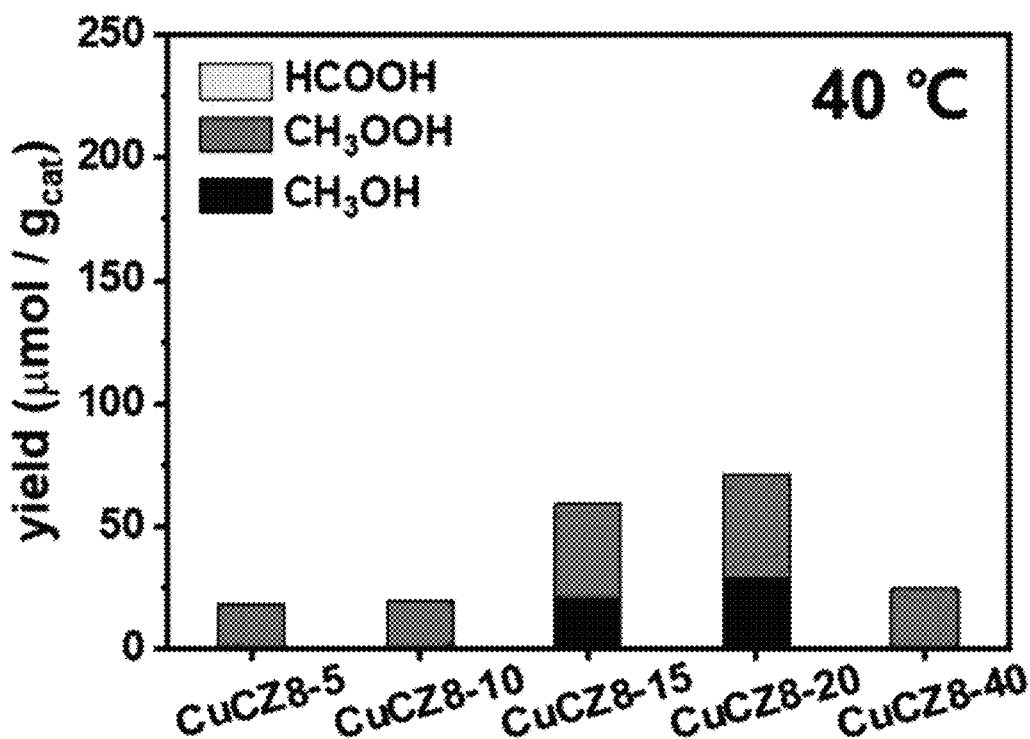
Figure 11C:
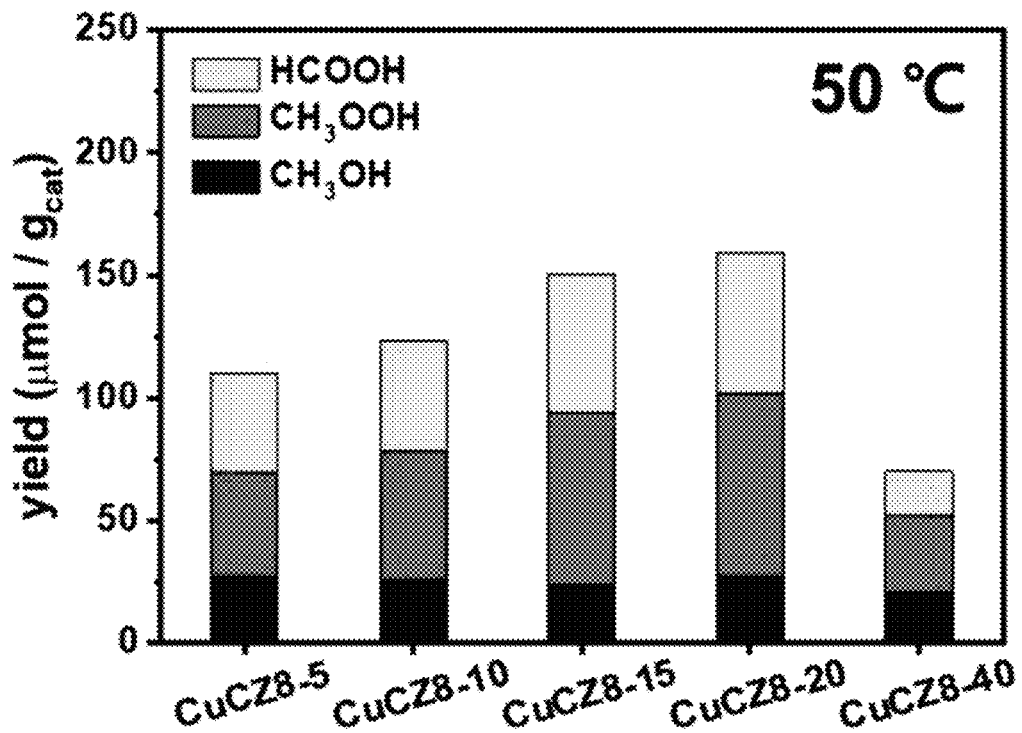
Figure 11D:
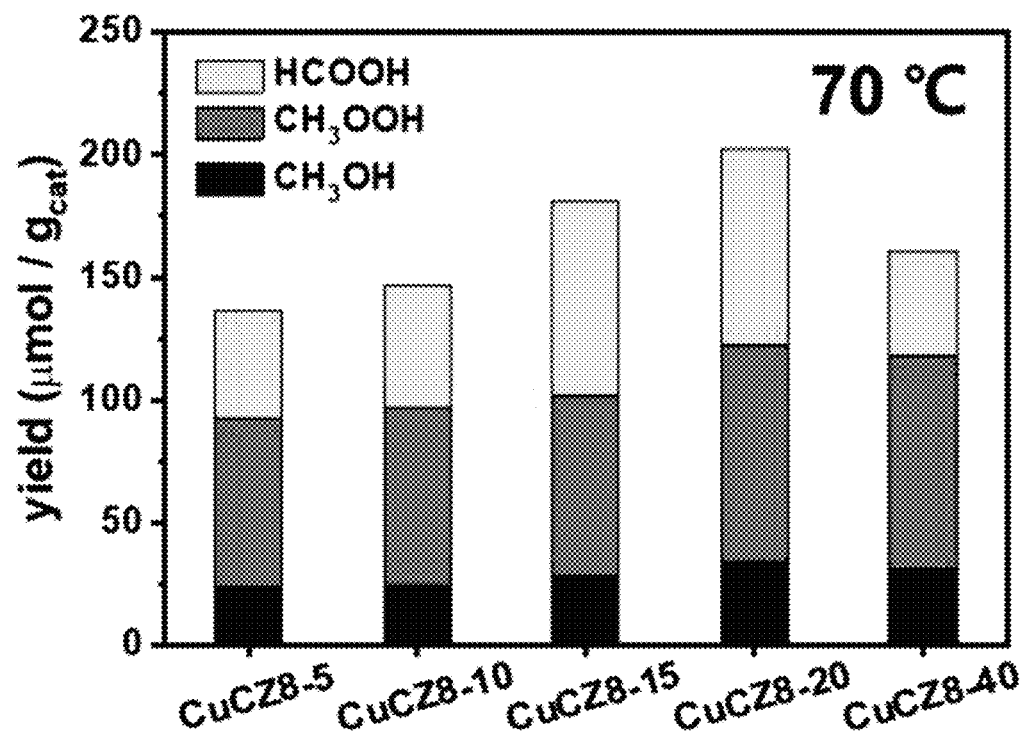

FIG. 10 shows methane conversion yields in the presence of the nanocatalysts prepared through carbonization at different temperatures in Example 4. Referring to FIG. 10, as the carbonization temperature increased, the methane conversion yield increased. In the presence of the nanocatalysts of Examples 4-2 and 4-3, methane gas was converted to methanol ($CH_3OH$) and methyl hydroperoxide ($CH_3OOH$) as liquid products in yields as high as 40 µmol/g. Particularly, the highest methane conversion yield (>50 µmol/g) was achieved in the presence of the nanocatalyst of Example 4-3. When the carbonization temperature exceeded 1000° C., the methane conversion yield was rather reduced due to excessive formation of copper nanoparticles.

Experimental Example 7: Analysis of Methane Conversion Yields Upon Reaction with Methane at Different Temperatures in the Presence of the Nanocatalysts Methane conversion yields were analyzed in the same manner as in Experimental Example 4, except that the reaction was carried out at different temperatures (30° C., 40° C., 50° C., and 70° C.) in the presence of the nanocatalysts prepared in Examples 1-5. The results are shown in FIGS. 11A to 11D.

FIGS. 11A to 11D show methane conversion yields at different temperatures (30° C., 40° C., 50° C., and 70° C.) in the presence of nanocatalysts prepared in Examples 1-5. Referring to FIGS. 11A to 11D, when the reaction temperatures were 30 and 40° C., methane gas was converted to only methanol ($CH_3OH$) and methyl hydroperoxide ($CH_3OOH$) as liquid products. In contrast, when the reaction temperature was ≥50° C., methane gas was peroxidized to formic acid (HCOOH). Particularly, the highest methane conversion yield was achieved in the presence of the nanocatalyst of Example 4 (CuCZ8-20). The methane conversion yield was reduced in the presence of the nanocatalyst of Example 5 (CuCZ8-40), indicating that a high content of Cu(0) nanoparticles negatively affected the methane conversion yield.

Experimental Example 8: Analysis of Methane Conversion Yields Upon Reaction with Methane for Different Times in the Presence of the Nanocatalyst Methane conversion yields and oxygen production rates were analyzed in the same manner as in Experimental Example 4, except that the reaction was carried out for different times (30 minutes, 1 h, 2 h, and 4 h) in the presence of the nanocatalyst prepared in Example 4. The results are shown in FIG. 12.

Figure 12:
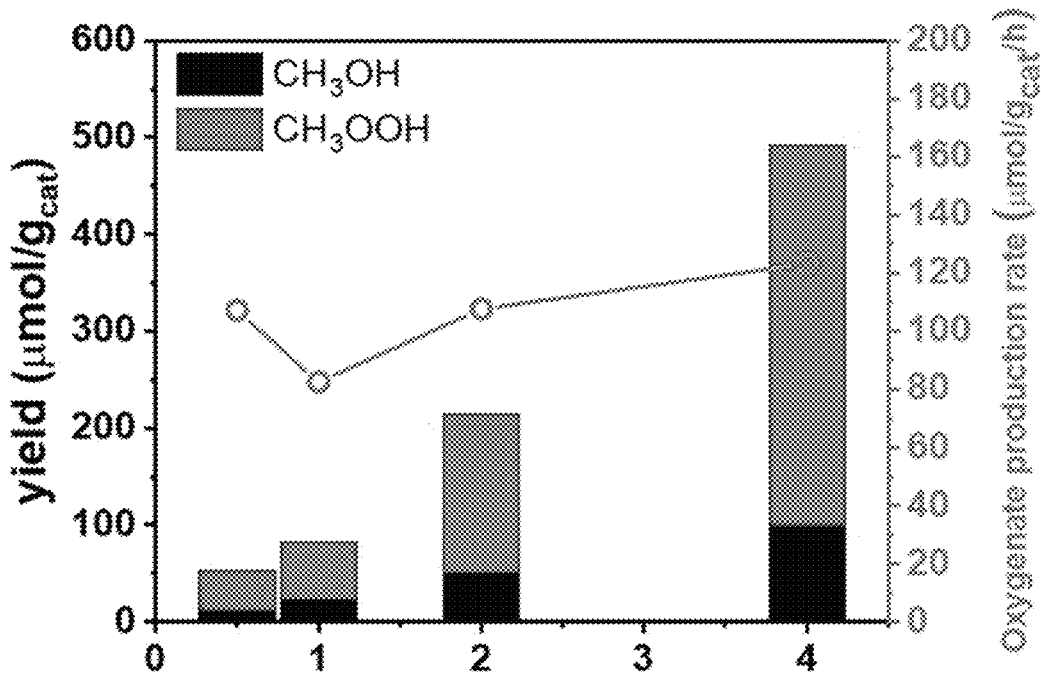
FIG. 12 shows methane conversion yields for different reactions times (30 minutes, 1 hour, 2 hours, and 4 hours) in the presence of a nanocatalyst prepared in Example 4.

FIG. 12 shows methane conversion yields for different reactions times (30 min, 1 h, 2 h, and 4 h) in the presence of the nanocatalyst prepared in Example 4. Referring to FIG. 12, the methane conversion yield increased in proportion to the reaction time. The oxygen production rate was lowest when the reaction time was 1 h, and thereafter, it gradually increased while maintaining the reactivity without yield reduction.

Experimental Example 9: Analysis of Methane Conversion Yields at Different Concentrations of Oxidizing Agent in the Presence of the Nanocatalyst Methane conversion yields and selectivities for methanol were analyzed in the same manner as in Experimental Example 4, except that the reaction was carried out at different concentrations (0.1, 0.5, 1, 2, and 4 M) of hydrogen peroxide ($H_2O_2$) as an oxidizing agent in the presence of the nanocatalyst prepared in Example 4. The results are shown in FIG. 13.

Figure 13:
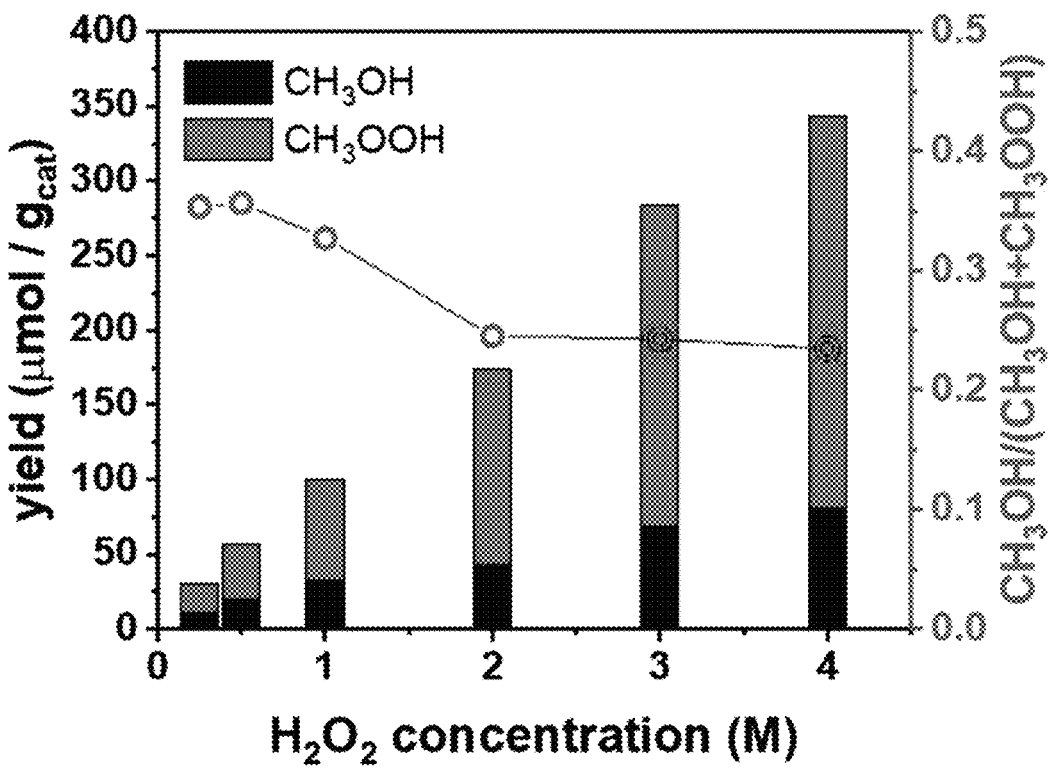
FIG. 13 shows methane conversion yields at different concentrations (0.1, 0.5, 1, 2, and 4 M) of hydrogen peroxide ($H_2O_2$) as an oxidizing agent in the presence of a nanocatalyst prepared in Example 4.

FIG. 13 shows methane conversion yields at different concentrations (0.1, 0.5, 1, 2, and 4 M) of hydrogen peroxide ($H_2O_2$) as an oxidizing agent in the presence of the nanocatalyst prepared in Example 4. Referring to FIG. 13, as the concentration of the oxidizing agent increased, the methane conversion yield increased proportionally but the selectivity for methanol as a liquid product from methane gas tended to decrease. Particularly, the highest selectivity for methanol (0.3-0.4) was achieved when the concentration of the oxidizing agent was 0.5 M.

What is claimed is:

1. A method for partial oxidation of methane, comprising: adding a porous nanocatalyst to water and dispersing the mixture by sonication to prepare a dispersion; and adding an oxidizing agent and methane gas to the dispersion and allowing the reaction for partial oxidation of the methane gas to proceed to form liquid products, wherein the porous nanocatalyst comprises a nitrogen-doped porous carbon structure and copper ions coordinated to nitrogen atoms present in the porous carbon structure wherein the porous carbon structure is formed by carbonizing a Zn-based zeolitic imidazole framework (ZIF-8), wherein a molar ratio of copper ions $Cu^{2+}/(Cu^{2+}+Zn^{2+})$ is in a range from 5 to 40.

2. The method according to claim 1, wherein the oxidizing agent is selected from the group consisting of hydrogen peroxide, sulfuric acid, nitric acid, iodic acid, tert-butylhydroxide, and mixtures thereof.

3. The method according to claim 1, wherein the oxidizing agent is added at a concentration of 0.1 to 4 M, relative to 5 mg of the nanocatalyst.

4. The method according to claim 1, wherein the methane gas is added at a pressure of 10 to 50 bar and the reaction is carried out at 25 to 45° C. for 10 minutes to 4 hours.

5. The method according to claim 1, wherein the liquid products are selected from methanol ($CH_3OH$), methyl hydroperoxide ($CH_3OOH$), and mixtures thereof.

6. The method according to claim 5, wherein the selectivity for the methanol ($CH_3OH/(CH_3OH+CH_3OOH)$) is 0.1 to 0.5.

7. The method according to claim 1, wherein the carbonization is performed under an inert gas atmosphere at 850 to 1100° C. for 1 to 5 hours.

8. The method according to claim 1, wherein the nanocatalyst is in the form of nanoparticles with an average particle size of 50 to 150 nm.

9. The method according to claim 1, wherein the nanocatalyst has a pore size of 0.4 to 1.1 nm and a specific surface area (BET) of 780 to 910 m$^2$/g and EXAFS spectroscopy of the nanocatalyst reveals that peaks corresponding to Cu—N (P1) and Cu—Cu(P2) appear at interatomic distances of 1.4 to 2.0 Å and 2.2 to 2.6 Å, respectively, and the ratio (P1/P2) of the intensity of the Cu—Cu peak (P2) to the intensity of the Cu—N peak (P1) is 0.3-1.4:1.

10. The method according to claim 1, wherein (i) the nanocatalyst is in the form of nanoparticles with an average particle size of 80 to 100 nm, (ii) the nanocatalyst has a pore size of 0.4 to 1.1 nm, (iii) the nanocatalyst has a specific surface area (BET) of 780 to 910 m$^2$/g, (iv) EXAFS spectroscopy of the nanocatalyst reveals that peaks corresponding to Cu—N(P1) and Cu—Cu(P2) appear at interatomic distances of 1.4 to 2.0 Å and 2.2 to 2.6 Å, respectively, and (v) the ratio (P1/P2) of the intensity of the Cu—Cu peak (P2) to the intensity of the Cu—N peak (P1) is 1.0-1.2:1.

11. The method according to claim 1, wherein the carbonization is performed under an inert gas atmosphere at 890 to 910° C. for 1.5 to 2.5 hours and the molar proportion of copper ions in the nanocatalyst is 19 to 22 mol %, as calculated by [copper ions ($Cu^{2+}$)/(copper ions ($Cu^{2+}$)+zinc ions ($Zn^{2+}$))]×100.

* * * * *